United States Patent [19]

Bayer et al.

[11] Patent Number: 4,578,224

[45] Date of Patent: * Mar. 25, 1986

[54] METHOD FOR PREPARATION OF SALTS OF N-PHOSPHONOMETHYLGLYCINE

[75] Inventors: Arthur C. Bayer, Yorktown Heights, N.Y.; Jeffrey D. Robbins, Berkeley; Donald J. Bowler, Concord, both of Calif.

[73] Assignee: Stauffer Chemical Company, Westport, Conn.

[*] Notice: The portion of the term of this patent subsequent to Aug. 23, 2000 has been disclaimed.

[21] Appl. No.: 622,427

[22] Filed: Jun. 20, 1984

Related U.S. Application Data

[63] Continuation of Ser. No. 435,122, Oct. 18, 1982, abandoned.

[51] Int. Cl.$^4$ .................................................. C07F 9/38
[52] U.S. Cl. ............................... 260/502.5 F; 548/312
[58] Field of Search ................................... 260/502.5 F

[56] References Cited

U.S. PATENT DOCUMENTS 3,288,846 11/1966 Irani et al. ..................... 260/502.5 E
4,128,558 12/1978 Hendricks et al. ........... 260/502.5 E
4,400,330 8/1983 Wong et al. .................... 260/502.5 F

*Primary Examiner*—J. E. Evans
*Attorney, Agent, or Firm*—Paul R. Martin

[57] ABSTRACT

Disclosed is a method for the preparation of salts of N-phosphonomethylglycine which comprises the steps of (a) reacting hydantoin or a 3-substituted hydantoin, a compound of the formula

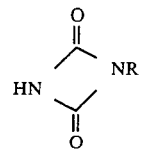

wherein R is selected from the group consisting of hydrogen, alkyl having from 1 to 10 carbon atoms, aryl having from 6 to 12 carbon atoms, alkylcarbonyl wherein the alkyl group has from 1 to 10 carbon atoms, and arylcarbonyl wherein the aryl group has from 6 to 12 carbon atoms, with paraformaldehyde in the presence of a low molecular weight carboxylic acid at a temperature and for a sufficient period of time to produce a mixture of intermediate products, including the 1-hydroxymethyl derivative of the starting hydantoin; (b) converting said 1-hydroxymethyl derivative to the 1-phosphonomethyl derivative by thereafter adding to the reaction mixture either (i) a substituted phosphorus compound selected from the group consisting of phosphorus trichloride, and phosphorus tribromide; or (ii) adding to the reaction mixture phosphorous acid and a anhydride selected from the group consisting acetic anhydride, propionic anhydride, butyric anhydride, or mixture thereof, and continuing said reaction at a temperature and for a sufficient period of time to cause completion of the reaction to form the 1-phosphonomethyl derivative; and (c) hydrolyzing the 1-phosphonomethylhydantoin product thus formed with a base selected from the group consisting of alkali metal or alkaline earth hydroxide, to produce a salt of N-phosphonomethylglycine.

9 Claims, No Drawings

METHOD FOR PREPARATION OF SALTS OF N-PHOSPHONOMETHYLGLYCINE

This application is a continuation of application Ser. No. 435,122, filed Oct. 18, 1982 now abandoned.

BACKGROUND OF THE INVENTION

This invention relates to a novel method for the preparation of N-phosphonomethylglycine, a compound which is a known herbicide and plant growth regulator.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way. There are a number of different types of herbicides presently sold commercially, and these fall into two general categories. The categories are pre-emergence and post-emergence herbicides. The pre-emergence herbicides are incorporated into the soil prior to the emergence of the weed plants from the soil, and the post-emergence herbicides are applied to plant surfaces after emergence of the weeds or other unwanted plants from the soil.

One of the earliest post-emergence herbicides used commercially was 2,4-D (2,4-dichlorophenoxyacetic acid). After a number of years of use of this and similar compounds such as 2,4,5-T (2,4,5-trichlorophenoxy acetic acid), it was found that certain decomposition products of these herbicides were long lasting and were not biodegradable. While there has been some dispute between governmental agencies and commercial interests regarding the effects of residual products of 2,4-D, 2,4,5-T and similar compounds, the agencies nevertheless restricted the use of these herbicides in the United States some years ago. Since that time, efforts have been made to develop herbicides which are biodegradable into harmless residues within a relatively short time after their application.

In field use it is normally applied in amounts of from 0.01 to about 20 pounds per acre, preferably from 2 to 6 pounds per acre.

N-Phosphonomethylglycine, and certain soluble salts thereof, can be made in a number of different ways. One such method, as described in U.S. Pat. No. 3,160,632 (Toy et al., Dec. 8, 1964) is to react N-phosphinomethylglycine (glycinemethylenephosphinic acid) with mercuric chloride in a water solvent at reflux temperature, and subsequently separating the reaction products. Another method is the reaction of ethyl glycinate with formaldehyde and diethylphosphite. The latter method is described in U.S. Pat. No. 3,799,758 (Franz, March 26, 1974). In addition, there is a whole series of patents, relating to N-phosphonomethylglycine, its salts, and derivatives thereof, described as being useful herbicides and plant growth regulators. Such additional patents relating to N-phosphonomethylglycine, methods of application, methods of preparation, salts, and derivatives, include U.S. Pat. No. 3,868,407, U.S. Pat. No. 4,197,254, and U.S. Pat. No. 4,199,354, among others.

Because of the importance of N-phosphonomethylglycine and certain salts as a herbicide, other methods of making the compounds are constantly being sought in order to provide improved or alternate methods of manufacture.

SUMMARY OF THE INVENTION

It has now been discovered that N-phosphonomethylglycine can be produced by:

(a) reacting hydantoin or a 3-substituted hydantoin, compounds of the formula

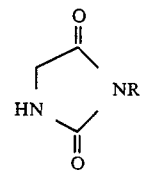

wherein R is selected from the group consisting of hydrogen, alkyl having from 1 to 10 carbon atoms, aryl having from 6 to 12 carbon atoms, alkylcarbonyl wherein the alkyl group has from 1 to 10 carbon atoms, and arylcarbonyl wherein the aryl group has from 6 to 12 carbon atoms, with paraformaldehyde in the presence of a low molecular weight carboxylic acid at a temperature and for a sufficient period of time to produce a mixture of intermediate products, including the 1-(hydroxymethyl) derivative;

(b) converting said 1-(hydroxymethyl) derivative to 1-phosphonomethylhydantoin by thereafter adding to the reaction mixture either (i) a substituted phosphorus compound selected from the group consisting of phosphorus trichloride, and phosphorus tribromide; or (ii) phosphorous acid and a carboxylic acid anhydride selected from the group consisting acetic anhydride, propionic anhydride, butyric anhydride, or a similar asymmetrical anhydride, and continuing said reaction at a temperature and for a sufficient period of time to cause completion of the reaction to form the 1-(phosphonomethyl) derivative; and (c) hydrolyzing said 1-(phosphonomethyl) derivative thus formed with an aqueous solution of a base selected from the group consisting of alkali metal or alkaline earth hydroxide, to produce a salt of N-phosphonomethylglycine; and (d) neutralizing said salt with a strong acid to produce the end product, N-phosphonomethylglycine.

The starting compound for use in the process of the invention is hydantoin, or a 3-substituted hydantoin, whose formula is indicated above. The preferred starting compound is the unsubstituted hydantoin, but 3-substituted hydantoins can be used, such as 3-methylhydantoin, 3-ethylhydantoin, and the like. Also suitable for use would be other alkyl-substituted hydantoins at the 3-position having from 1 to 20 carbon atoms, the aryl-substituted hydantoins at the 3-position having from 6 to 12 carbon atoms, the alkylcarbonyl-substituted hydantoins at the 3-position having from 1 to 10 carbon atoms in the alkyl group, and the arylcarbonylsubstituted hydantoins at the 3-position having from 6 to 12 carbon atoms in the aryl group. The substituted compounds are less preferred, however, because of their greater cost.

Paraformaldehyde is used in the process of the invention in order to eliminate water from the initial steps of the reaction. Aqueous formalin is obviously unsuitable because water is undesirable.

Acetic acid is the preferred low molecular weight carboxylic acid for use in step (a) of the process of the invention. Other suitable low molecular weight carboxylic acids which can be used include propanoic acid and butanoic acid, for example.

The most preferred substituted phosphorus compound for use in the above process is phosphorus trichloride. Other phosphorus compounds which can be used include phosphorus tribromide.

The preferred base for use in step (c) of the process is sodium hydroxide, however, other bases such as potassium hydroxide or barium hydroxide could also be used.

The preferred anhydride for use in step (b) (ii) is acetic anhydride. Other suitable anhydrides which can be used, however, include propionic anhydride, butyric anhydride, and mixed anhydrides of acetic, propionic, and butyric acids.

The preferred acid for use in step (d) of the process of the invention is hydrochloric acid, however, other acids such as hydrobromic acid, hydriodic acid, sulfuric acid, and phosphoric acid, can be used. These acids may be described as relatively strong protic acids and any other acids falling within that purview would be suitable for use also.

Using the preferred compounds the overall reaction for the process of the invention can be presented as follows:

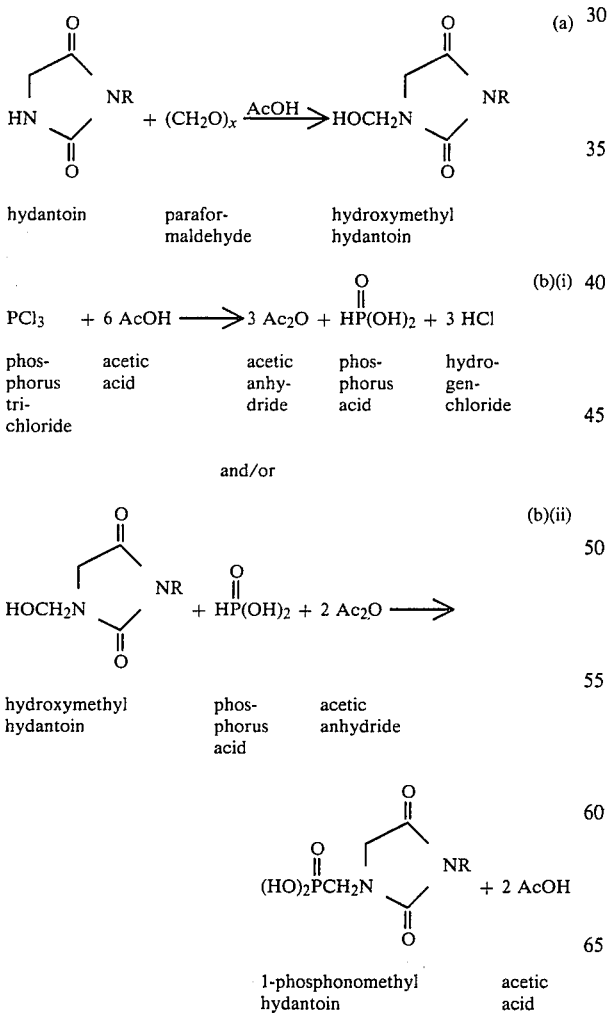

In the process of the invention, the starting hydantoin compound, paraformaldehyde, and phosphorus trichloride are all used at approximately stoichiometric amounts in a ratio of 1:1:1. The low molecular weight carboxylic acid is generally present in excess. The same applies for the sodium hydroxide used in step (c), and in step (d), sufficient acid is used to bring the pH of the reaction mixture down to approximately 1.4, which is the pH at which the end product, N-phosphonomethylglycine, crystallizes most efficiently out of solution.

The first step of the reaction is conducted at reflux temperature, and when acetic acid is used as the carboxylic acid, this temperature ranges from approximately 115° to 120° C. The hydantoin and formaldehyde are refluxed for approximately 45 minutes. However, the exact amount of time is not critical.

The phosphorus trichloride in step (b) is initially added to the reaction mixture at room temperature and is then heated to reflux. Hydrogen chloride is evolved as the reactants are heated, thus, the temperature is raised slowly over a period of approximately 50 minutes until reflux is reached, again being approximately between 115° and 120° C. After the reflux temperature is reached, the reactants are refluxed for an additional 20 minutes to insure completion of the reaction.

While not shown in the formulas, water can optionally be added at the end of step (b) while the reactants are at reflux temperature. After water is added, the reaction mixture is refluxed for approximately 2 hours. The bulk of the carboxylic acid-water solvent mixture is then removed by evaporation at reduced pressure.

The base of step (d) is added at room temperature and the hydrolysis step is conducted at reflux (approximately 102° C.) for a period of approximately 24 hours, when sodium hydroxide is used as the base of choice.

It has been found that the yield of phosphonomethylhydantoin can be improved if acetic anhydride or acetyl chloride is added at the very beginning of step (a) along with the paraformaldehyde and hydantoin. The reason for the improvement in yield is not exactly known. However, this improvement is only obtained when hydantoin is used rather than a 3-substituted derivative. Thus, when hydantoin is used, the preferred process includes the addition of acetic anhdyride or acetyl chloride along with the other components in step (a) at the beginning of the reaction.

This invention will be better understood by reference to the specific example which follows, which serves to illustrate the instant invention.

EXAMPLE I

Preparation of N-Phosphonomethylglycine Trisodiuum Salt

A 500 milliliter (ml), round-bottom flask was was equipped with a thermometer, condenser, magnetic stirrer and heating mantle. Into this flask was charged, under nitrogen, 10 grams (g) (0.10 mole) of hydantoin and 3.2 g (0.10 mole) of paraformaldehyde (ca. 95% pure), along with 60 ml of anhydrous acetic acid. The mixture was then heated to reflux and maintained at reflux for 45 minutes. Thereafter, the reaction mixture was cooled to room temperature and at that time 13.8 g (0.10 mole) of phosphorus trichloride was charged all at once. An exotherm occured. The reaction mixture was slowly heated to reflux while gas evolved. During the heating period a white precipitate (1,1'-methane-bis(-hydantoin)) formed and then redissolved. The reaction mixture was kept at reflux for approximately 2 hours, and thereafter 150 ml of water was added and the mixture refluxed for an additional 1.5 hours. The mixture was then vacuum stripped at 70° C. to give crude 1-(phosphonomethyl)hydantoin as 24.4 g of a viscous pink oil. The crude product was assayed quantitatively by high performance liquid chromatography (hplc) and found to be 43.7% pure. The yield, then, was 10.7 g, 56% of theory.

EXAMPLE II

Preparation of N-phosphonomethylglycine from 1-(phosphonomethyl)hydantoin

Crude 1-(phosphonomethyl)hydantoin was prepared as described above, induced to crystallize at low temperature, and then partially purified by digestion in refluxing isopropyl alcohol-ether (1:5). The purified material was assayed by hplc on an anion exchange column and found to be 75.3 weight % pure. A solution of 1.94 g (7.53 mmole) of this material and 50 ml 2N aqueous NaOH was heated at reflux (102° C.0) for 24 hours. The cooled reaction mixture was assayed by hplc analysis on an anion exchange column and found to contain 7.65±0.40 mmole of N-phosphonomethylglycine trisodium salt. The yield of the salt, therefore, was approximately 100%.

The solution of the salt was acidified with 12N HCl to pH 1.5 and filtered to remove precipitated white solids (probably silicic acid). The filtrate was chilled, seeded, and allowed to stand at ca 5° C. for a few days. A precipitate of crystalline phosphonomethylglycine formed and was isolated by filtration, washing, and drying. The yield was 0.48 g (1.84 mmol, 38% based on 1-phosphonomethylglycine). The nmr and ir spectra of the product were identical to those of authentic material.

EXAMPLE III

Preparation of 1-(Phosphonomethyl)hydantoin

The preparation of 1-(phosphonomethyl)hydantoin was carried out by a slight modification of the method of Example I. The only change made was that 11.2 g (0.110 mole) of acetic anhydride was added at the outset. The yield of 1-(phosphonomethyl)hydantoin was 76% of the theoretical amount.

EXAMPLE IV

Preparation of 1-(Phosphonomethyl)hydantoin

The preparation was carried out by a slight modification of the method of Example I. The change made was that 8.6 g (0.110 mole) of acetyl chloride was added at the outset. This made it necessary to heat the initial mixture with caution, because a strongly exothermic reaction, accompanied by gas evoluation, occurred when heating was begun. In all other respects the method used was the same as that of Example I. The yield of 1-(phosphonomethyl)hydantoin was 75% of the theoretical amount.

EXAMPLE V

Preparation of 1-(Phosphonomethyl)hydantoin

A 500 ml round-bottom flask was equipped with a thermometer, condenser, magnetic stirrer, and heating mantle. Into the flask was charged, under nitrogen, 10.0 g (0.100 mole) of hydantoin, 3.2 g (0.10 mole) of paraformaldehyde (purity: ca 95%), and 60 ml of anhydrous acetic acid. The resulting mixture was heated at reflux for 0.75 hour and then cooled. To the resulting clear solution was added 8.5 g (0.100 mole) of 97% phosphorous acid and 30.6 g (0.300 mole) of acetic anhydride. The reaction mixture was heated to reflux over 1.2 hours and held at reflux for another 0.1 hour. (A white solid precipitated early in the heating period and then redissolved toward the end.) The reaction mixture was cooled somewhat, and 150 ml of water was added to it. The resulting solution was heated at reflux for 2.0 hours, cooled, and vacuum stripped at 70° C. to give 21.4 g of crude 1-(phosphonomethyl)hydantoin as an oil. Quantitative analysis by hplc showed the yield of 1-(phosphonomethyl) hydantoin to be 46%.

EXAMPLE VI

N-Phosphonomethylglycine Trisodium Salt

Crude 3-methyl-1-(phosphonomethyl)hydantoin (6.54 g) was prepared by the method of Example I from 2.85 g (0.025 mole) of 3-methylhydantoin, 0.8 g (ca 0.025 mole) of paraformaldehyde, 11 ml of anhydrous acetic acid, and 3.5 g (0.024 mole) of phosphorus trichloride. A portion (5.56 g) of the crystalline crude product was dissolved in 10 ml of water, and the solution was basified to pH 10.7 with 20% aqueous sodium hydroxide. To the resulting solution was added 200 ml of 2N sodium hydroxide. The solution obtained was heated at reflux for 24 hours, cooled, weighed and quantitatively assayed by hplc for N-phosphonomethylglycine trisodium salt. The yield was found to be 72% of the theoretical amount.

In carrying out the process of the invention, it should be noted that after phosphorus trichloride is added to the reaction mixture, a white precipitate normally crystallizes out, but is later dissolved when the solution is heated to reflux temperature. The crystalline compound has been isolated and found to be 1,1'-methane-bis-hydantoin. It has been found that this substance is converted to 1-(phosphonomethyl)hydantoin (49% yield) when it is treated with phosphorus trichloride and acetic acid and the reaction mixture is worked up in the usual way.

In step (b) of the process of the invention, it makes little difference whether sub-section (i) or (ii) is followed because the end product is the same in both instances. Thus, when the phosphorus trichloride is added and used in conjunction with acetic acid, the intermediate product produced is 1-(phosphonomethyl)hydantoin, while when section (a) (ii) is used, and acetic anhydride and phosphorous acid are combined, the product is still 1-(phosphonomethyl)hydantoin. It is believed that the phosphorus trichloride and acetic acid react in solution to give phosphorous acid and acetic anhydride, the components used in stap (b) (ii) as shown above.

It will be recognized by those skilled in the art that variations in the quantities of reactants, temperatures used, mole ratios used, and time of reaction can be made in the method of the invention without departing from the spirit and scope of the appended claims.

What is claimed is:

1. A method for the preparation of salts of N-phosphonomethylglycine which comprises the steps of:
   (a) reacting hydantoin or a 3-substituted hydantoin, compounds of the general formula

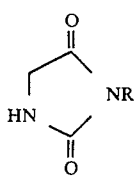

wherein R is selected from the group consisting of hydrogen, alkyl having from 1 to 10 carbon atoms, aryl having from 6 to 12 carbon atoms, alkylcarbonyl wherein the alkyl group has from 1 to 10 carbon atoms, and arylcarbonyl wherein the aryl group has from 6 to 12 carbon atoms, with paraformaldehyde in the presence of a low molecular weight carboxylic acid at a temperature and for a sufficient period of time to produce a mixture of intermediate products, including the 1-(hydroxymethyl) derivative of the starting hydantoin
   (b) converting said 1(hydroxymethyl) derivative to the 1-phosphonomethyl derivative by thereafter adding to the reaction mixture either
      (i) a substituted phosphorus compound selected from the group consisting of phosphorus trichloride, and phosphorus tri-bromide; or
      (ii) adding to the reaction mixture phosphorus acid and an anhydride selected from the group consisting acetic anhydride, propionic anhydride, butyric anhydride, or a similar asymmetrical anhydride and
   continuing said reaction at a temperature and for a sufficient period of time to cause completion of the reaction to form the 1-phosphonomethyl derivative; and
   (c) hydrolyzing the 1-phosphonomethylhydantoin product thus formed with a base selected from the group consisting of alkali metal or alkaline earth hydroxide, to produce a salt of N-phosphonomethylglycine.

2. The method of claim 1 in which said substituted phosphorus compound is selected from the group consisting of phosphorus trichloride, and phosphorus tri-bromide.

3. The method of claim 1 in which said low molecular weight carboxylic acid is selected from the group consisting of acetic, propanoic and butanoic acid.

4. The method of claim 1 in which said hydantoin, paraformaldehyde and substituted phosphorus compounds are used in approximately stoichiometric amounts and said carboxylic acid is used in excess.

5. The method of claim 1 in which said hydantoin is 3-methyl hydantoin.

6. The method of claim 1 in which said paraformaldehyde is used in excess relative to said hydantoin.

7. The method of claim 1 in which said base of step (c) is selected from the group consisting of alkaline metal or alkaline earth hydroxides.

8. The method of claim 1 in which acetyl chloride or acetic anhydride is added along with the other reactants in step (a) of the process.

9. The method of claim 1 in which step (b) is accomplished by adding to the reaction mixture phosphorous acid and an anhydride selected from the group consisting of acetic anhydride, propionic anhydride, butyric anhydride, or mixtures thereof.

* * * * *